(12) United States Patent
Xia et al.

(10) Patent No.: US 9,388,170 B2
(45) Date of Patent: Jul. 12, 2016

(54) SUBSTITUTED AMINOQUINAZOLINES USEFUL AS KINASES INHIBITORS

(71) Applicant: TELIGENE LTD., Suzhou (CN)

(72) Inventors: Xiaoyang Xia, Thousand Oaks, CA (US); Dawei Zhang, Thousand Oaks, CA (US)

(*) Notice: Subject to any disclaimer, the term of this patent is extended or adjusted under 35 U.S.C. 154(b) by 0 days.

(21) Appl. No.: 14/399,510

(22) PCT Filed: May 7, 2013

(86) PCT No.: PCT/CN2013/075244
§ 371 (c)(1),
(2) Date: Nov. 6, 2014

(87) PCT Pub. No.: WO2013/166952
PCT Pub. Date: Nov. 14, 2013

(65) Prior Publication Data
US 2015/0126539 A1  May 7, 2015

Related U.S. Application Data

(60) Provisional application No. 61/687,981, filed on May 7, 2012, provisional application No. 61/848,413, filed on Jan. 4, 2013.

(51) Int. Cl.
*A61K 31/517* (2006.01)
*C07D 405/12* (2006.01)
*A61K 45/06* (2006.01)

(52) U.S. Cl.
CPC ............ *C07D 405/12* (2013.01); *A61K 31/517* (2013.01); *A61K 45/06* (2013.01)

(58) Field of Classification Search
CPC ..................................................... C07D 405/12
See application file for complete search history.

(56) References Cited

U.S. PATENT DOCUMENTS 8,735,409 B2   5/2014  Zhang et al.

FOREIGN PATENT DOCUMENTS

CN  WO2012136099 A1  10/2012
WO  WO2011084796 A2   7/2011

*Primary Examiner* — Brian McDowell
(74) *Attorney, Agent, or Firm* — Feng Tian

(57) ABSTRACT

The present invention is directed to novel quinazolines, their derivatives, pharmaceutically acceptable salts, solvates and hydrates thereof. The compounds and compositions of the present invention have protein kinases inhibitory activities and are expected to be useful for the treatment of protein kinases mediated diseases and conditions.

9 Claims, No Drawings

SUBSTITUTED AMINOQUINAZOLINES USEFUL AS KINASES INHIBITORS

CROSS REFERENCE

The application is a 35 U.S.C. §371 national stage filing of International Patent Application PCT/CN2013/075244 (published as WO 2013/166952 A1), filed May 7, 2013, which is entitled to priority pursuant to 35 U.S.C. §119(e) to U.S. Provisional Application Nos. 61/687,981, filed May 7, 2012 and 61/848,413 filed Jan. 4, 2013. The entire disclosures of the afore-mentioned patents are hereby incorporated by reference in their entirety.

FIELD OF THE INVENTION

The present invention is directed to inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Due to their activity in numerous cellular processes, protein kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy. The human epidermal growth factor receptor (HER) tyrosine kinase family consists of four structurally related cellular receptors: the epidermal growth factor receptor (EGFR; HER1), HER2 (ErbB2), HER3 (ErbB3), and HER4.

Quinazolines are a known class of kinase inhibitors with utility for the treatment of cancer, angiogenesis disorders, and inflammatory disorders. To this end, attempts have been made to identify small molecules which act as protein kinase inhibitors. For example, quinazoline derivatives (PCT WO 00177104; US20050250761; WO2004069791) have been described as HER kinase inhibitors. EGFR inhibitors Erlotinib and Gefitinib as well as the dual EGFR/HER2 inhibitor Lapatinib are FDA-approved cancer drugs that are effective against multiple solid tumor cancers. However, their effectiveness is also limited by the drug resistance that frequent emerges following treatment.

Thus, the compounds that can inhibit protein kinases such as HER kinases activity with improved efficacy or overcoming drug resistance are highly desired.

SUMMARY OF THE INVENTION

The present invention provides compounds of Formula I:

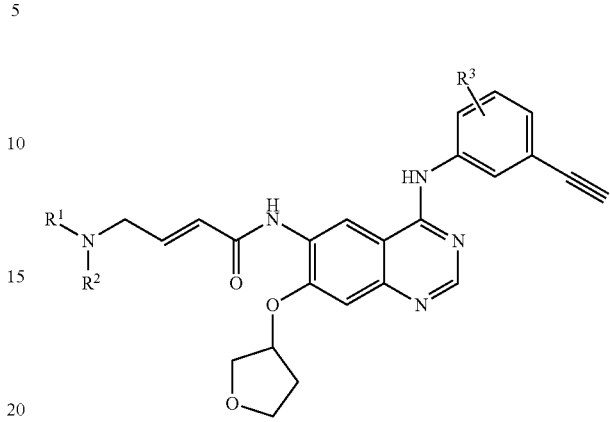

or a pharmaceutically acceptable salt, solvate or a prodrug or a stereoisomer or a tautomer or metabolite thereof, wherein $R^1$ and $R^2$ are independently selected from hydrogen, and $C_1$-$C_3$ alkyl;
$R^3$ is selected from hydrogen, halogen, $C_1$-$C_3$ alkyl, CN, and $CF_3$.

The present invention further provides pharmaceutical compositions comprising a compound of Formula I described above and a pharmaceutically acceptable carrier.

The present invention further provides methods for regulating the kinase signaling transduction comprising administrating to a mammalian subject a therapeutically effective amount of any of the compounds of Formula I described above.

DETAILED DESCRIPTION OF THE INVENTION

In some embodiments of the present invention, there are provided compounds of Formula I:

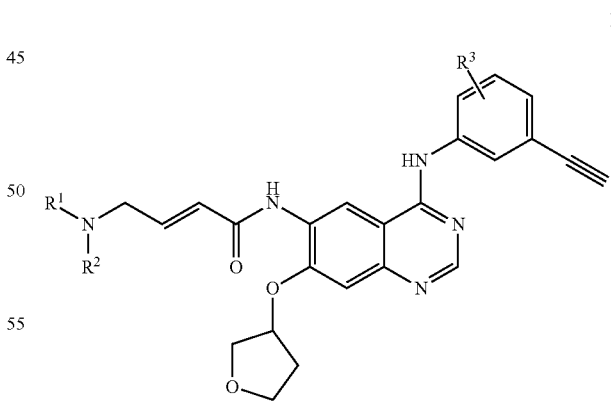

or a pharmaceutically acceptable salt, solvate or a prodrug or a stereoisomer or a tautomer or metabolite thereof, wherein $R^1$ and $R^2$ are independently selected from hydrogen, and $C_1$-$C_3$ alkyl;
$R^3$ is selected from hydrogen, halogen, $C_1$-$C_3$ alkyl, CN, and $CF_3$.

In certain embodiments, $R^1$ or $R^2$ is hydrogen. In other embodiments, both $R^1$ and $R^2$ are methyl or ethyl. In other embodiments, $R^3$ is F. In some embodiments, $R^3$ is methyl. In other embodiments $R^3$ is hydrogen. In the preferred embodiments, $R^1$ and $R^2$ are independently selected from the group consisting of methyl and ethyl; and $R^3$ is selected from the group consisting of hydrogen, methyl, Cl, and F. In the most preferred embodiment, $R^1$ and $R^2$ are both ethyl; and $R^3$ is hydrogen, methyl, Cl, or F. In other embodiments, the compound of Formula I is in the form of pharmaceutically acceptable salt. In some embodiments, the compound of Formula I is in the form of a solvate. In other embodiments, the compound of Formula I is in the form of a metabolite. In other embodiments, the compound of Formula I is in the form of a prodrug. In some embodiments, the compound of Formula I is a stereoisomer. In other embodiments, the compound of Formula I is a tautomer. In another embodiment, the deuterium enrichment in compounds of Formula I is at least about 1%.

In certain embodiments, there are provided compounds without limitation selected from the group consisting of:

(RS,E)-4-(dimethylamino)-N-(4-((3-ethynylphenyl)amino)-7-((tetrahydrofuran-3-yl)oxy)quinazolin-6-yl)but-2-enamide;

(RS,E)-4-(diethylamino)-N-(4-((3-ethynylphenyl)amino)-7-((tetrahydrofuran-3-yl)oxy)quinazolin-6-yl)but-2-enamide;

(RS,E)-4-(dipropylamino)-N-(4-((3-ethynylphenyl)amino)-7-((tetrahydrofuran-3-yl)oxy)quinazolin-6-yl)but-2-enamide;

(RS,E)-4-(ethyl(methyl)amino)-N-(4-((3-ethynylphenyl)amino)-7-((tetrahydrofuran-3-yl)oxy)quinazolin-6-yl)but-2-enamide;

(RS,E)-4-(dimethylamino)-N-(4-((3-ethynyl-4-fluorophenyl)amino)-7-((tetrahydrofuran-3-yl)oxy)quinazolin-6-yl)but-2-enamide;

(RS,E)-N-(4-((4-chloro-3-ethynylphenyl)amino)-7-((tetrahydrofuran-3-yl)oxy)quinazolin-6-yl)-4-(dimethylamino)but-2-enamide;

(RS,E)-4-(dimethylamino)-N-(4-((3-ethynyl-5-methylphenyl)amino)-7-((tetrahydrofuran-3-yl)oxy)quinazolin-6-yl)but-2-enamide;

(RS,E)-4-(dimethylamino)-N-(4-((5-ethynyl-2-fluorophenyl)amino)-7-((tetrahydrofuran-3-yl)oxy)quinazolin-6-yl)but-2-enamide;

(RS,E)-4-(dimethylamino)-N-(4-((3-ethynyl-5-(trifluoromethyl)phenyl)amino)-7-((tetrahydrofuran-3-yl)oxy)quinazolin-6-yl)but-2-enamide;

(S,E)-4-(dimethylamino)-N-(4-((3-ethynylphenyl)amino)-7-((tetrahydrofuran-3-yl)oxy)quinazolin-6-yl)but-2-enamide;

(R,E)-4-(dimethylamino)-N-(4-((3-ethynylphenyl)amino)-7-((tetrahydrofuran-3-yl)oxy)quinazolin-6-yl)but-2-enamide;

(S,E)-4-(diethylamino)-N-(4-((3-ethynylphenyl)amino)-7-((tetrahydrofuran-3-yl)oxy)quinazolin-6-yl)but-2-enamide;

(R,E)-4-(diethylamino)-N-(4-((3-ethynylphenyl)amino)-7-((tetrahydrofuran-3-yl)oxy)quinazolin-6-yl)but-2-enamide;

(S,E)-4-(dipropylamino)-N-(4-((3-ethynylphenyl)amino)-7-((tetrahydrofuran-3-yl)oxy)quinazolin-6-yl)but-2-enamide;

(R,E)-4-(dipropylamino)-N-(4-((3-ethynylphenyl)amino)-7-((tetrahydrofuran-3-yl)oxy)quinazolin-6-yl)but-2-enamide;

(S,E)-4-(ethyl(methyl)amino)-N-(4-((3-ethynylphenyl)amino)-7-((tetrahydrofuran-3-yl)oxy)quinazolin-6-yl)but-2-enamide;

(S,E)-4-(dimethylamino)-N-(4-((3-ethynyl-4-fluorophenyl)amino)-7-((tetrahydrofuran-3-yl)oxy)quinazolin-6-yl)but-2-enamide;

(S,E)-N-(4-((4-chloro-3-ethynylphenyl)amino)-7-((tetrahydrofuran-3-yl)oxy)quinazolin-6-yl)-4-(dimethylamino)but-2-enamide;

(S,E)-4-(dimethylamino)-N-(4-((3-ethynyl-5-methylphenyl)amino)-7-((tetrahydrofuran-3-yl)oxy)quinazolin-6-yl)but-2-enamide;

(S,E)-4-(dimethylamino)-N-(4-((5-ethynyl-2-fluorophenyl)amino)-7-((tetrahydrofuran-3-yl)oxy)quinazolin-6-yl)but-2-enamide; and (S,E)-4-(dimethylamino)-N-(4-((3-ethynyl-5-(trifluoromethyl)phenyl)amino)-7-((tetrahydrofuran-3-yl)oxy)quinazolin-6-yl)but-2-enamide;

(S,E)-4-(ethylamino)-N-(4-((3-ethynylphenyl)amino)-7-((tetrahydrofuran-3-yl)oxy)quinazolin-6-yl)but-2-enamide;

(S,E)-4-(diethylamino)-N-(4-((3-ethynyl-4-fluorophenyl)amino)-7-((tetrahydrofuran-3-yl)oxy)quinazolin-6-yl)but-2-enamide;

(S,E)-N-(4-((4-chloro-3-ethynylphenyl)amino)-7-((tetrahydrofuran-3-yl)oxy)quinazolin-6-yl)-4-(diethylamino)but-2-enamide;

(S,E)-N-(4-((4-cyano-3-ethynylphenyl)amino)-7-((tetrahydrofuran-3-yl)oxy)quinazolin-6-yl)-4-(diethylamino)but-2-enamide;

(S,E)-4-(diethylamino)-N-(4-((3-ethynyl-4-(trifluoromethyl)phenyl)amino)-7-((tetrahydrofuran-3-yl)oxy)quinazolin-6-yl)but-2-enamide;

(S,E)-4-(diethylamino)-N-(4-((3-ethynyl-4-methylphenyl)amino)-7-((tetrahydrofuran-3-yl)oxy)quinazolin-6-yl)but-2-enamide;

(S,E)-4-(diethylamino)-N-(4-((3-ethynyl-5-fluorophenyl)amino)-7-((tetrahydrofuran-3-yl)oxy)quinazolin-6-yl)but-2-enamide;

(S,E)-N-(4-((3-chloro-5-ethynylphenyl)amino)-7-((tetrahydrofuran-3-yl)oxy)quinazolin-6-yl)-4-(diethylamino)but-2-enamide;

(S,E)-4-(diethylamino)-N-(4-((3-ethynyl-5-methylphenyl)amino)-7-((tetrahydrofuran-3-yl)oxy)quinazolin-6-yl)but-2-enamide;

(S,E)-4-(diethylamino)-N-(4-((3-ethynyl-5-(trifluoromethyl)phenyl)amino)-7-((tetrahydrofuran-3-yl)oxy)quinazolin-6-yl)but-2-enamide;

(S,E)-N-(4-((3-cyano-5-ethynylphenyl)amino)-7-((tetrahydrofuran-3-yl)oxy)quinazolin-6-yl)-4-(diethylamino)but-2-enamide;

(S,E)-4-(ethylamino)-N-(4-((3-ethynyl-5-(trifluoromethyl)phenyl)amino)-7-((tetrahydrofuran-3-yl)oxy)quinazolin-6-yl)but-2-enamide;

(S,E)-4-(diethylamino)-N-(4-((5-ethynyl-2-fluorophenyl)amino)-7-((tetrahydrofuran-3-yl)oxy)quinazolin-6-yl)but-2-enamide;

(S,E)-N-(4-((2-chloro-5-ethynylphenyl)amino)-7-((tetrahydrofuran-3-yl)oxy)quinazol in-6-yl)-4-(diethylamino)but-2-enamide;

(S,E)-4-(diethylamino)-N-(4-((5-ethynyl-2-(trifluoromethyl)phenyl)amino)-7-((tetrahydrofuran-3-yl)oxy)quinazolin-6-yl)but-2-enamide;

(S,E)-N-(4-((2-cyano-5-ethynylphenyl)amino)-7-((tetrahydrofuran-3-yl)oxy)quinazolin-6-yl)-4-(diethylamino)but-2-enamide;

(S,E)-4-(diethylamino)-N-(4-((5-ethynyl-2,4-difluorophenyl)amino)-7-((tetrahydrofuran-3-yl)oxy)quinazolin-6-yl)but-2-enamide;

(S,E)-N-(4-((4-chloro-5-ethynyl-2-fluorophenyl)amino)-7-((tetrahydrofuran-3-yl)oxy)quinazolin-6-yl)-4-(ethylamino)but-2-enamide;

(S,E)-4-(diethylamino)-N-(4-((5-ethynyl-2,3-difluorophenyl)amino)-7-((tetrahydrofuran-3-yl)oxy)quinazolin-6-yl)but-2-enamide;

(S,E)-4-(diethylamino)-N-(4-((3-ethynyl-4,5-difluorophenyl)amino)-7-((tetrahydrofuran-3-yl)oxy)quinazolin-6-yl)but-2-enamide;

(S,E)-4-(ethylamino)-N-(4-((3-ethynyl-4-fluorophenyl)amino)-7-((tetrahydrofuran-3-yl)oxy)quinazolin-6-yl)but-2-enamide;

(5,E)-N-(4-((4-chloro-3-ethynylphenyl)amino)-7-((tetrahydrofuran-3-yl)oxy)quinazolin-6-yl)-4-(ethylamino)but-2-enamide;

(S,E)-4-(ethyl(methyl)amino)-N-(4-((3-ethynyl-4-(trifluoromethyl)phenyl)amino)-7-((tetrahydrofuran-3-yl)oxy)quinazolin-6-yl)but-2-enamide;

(S,E)-N-(4-((4-cyano-3-ethynylphenyl)amino)-7-((tetrahydrofuran-3-yl)oxy)quinazolin-6-yl)-4-(ethylamino)but-2-enamide;

and some of their chemical structures are listed as follows:

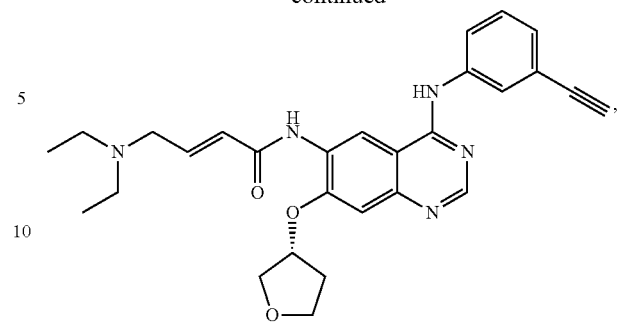

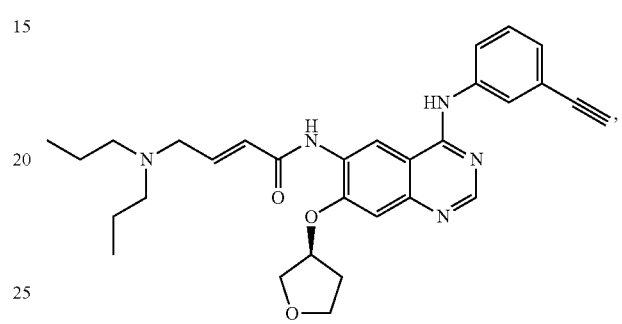

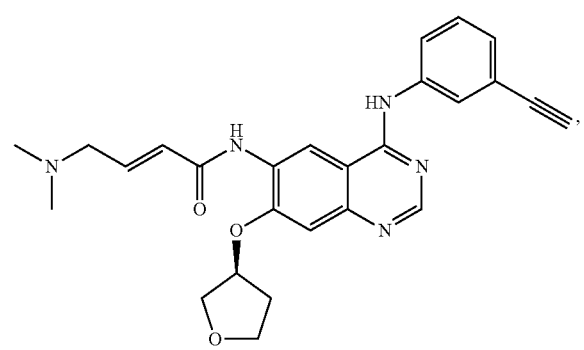

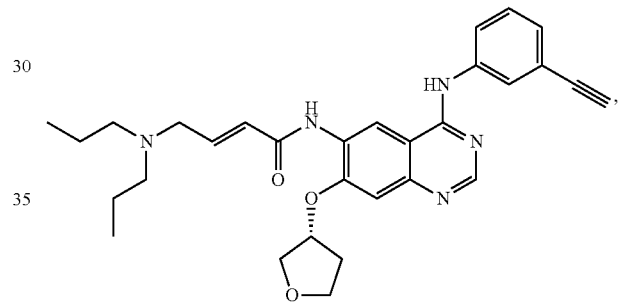

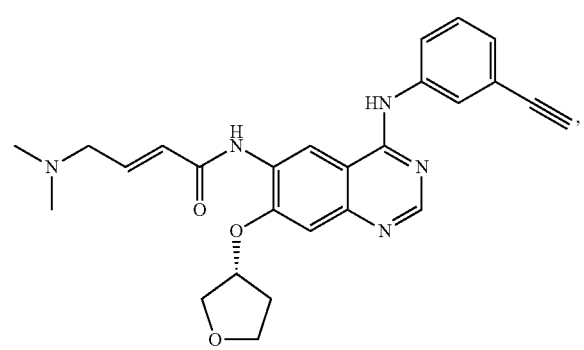

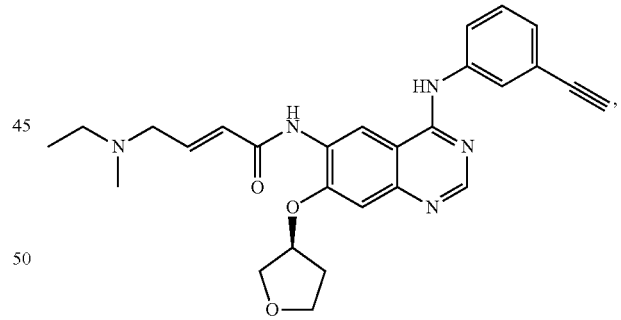

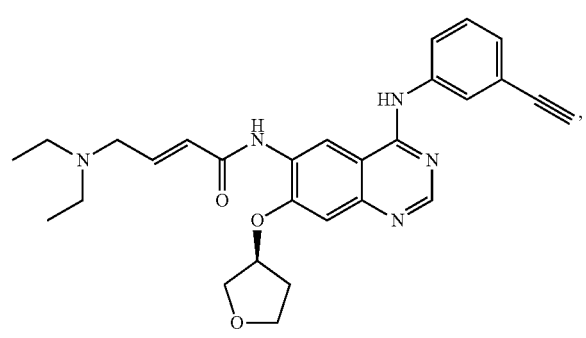

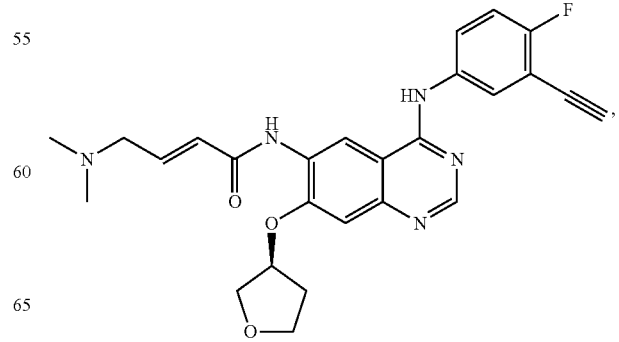

-continued

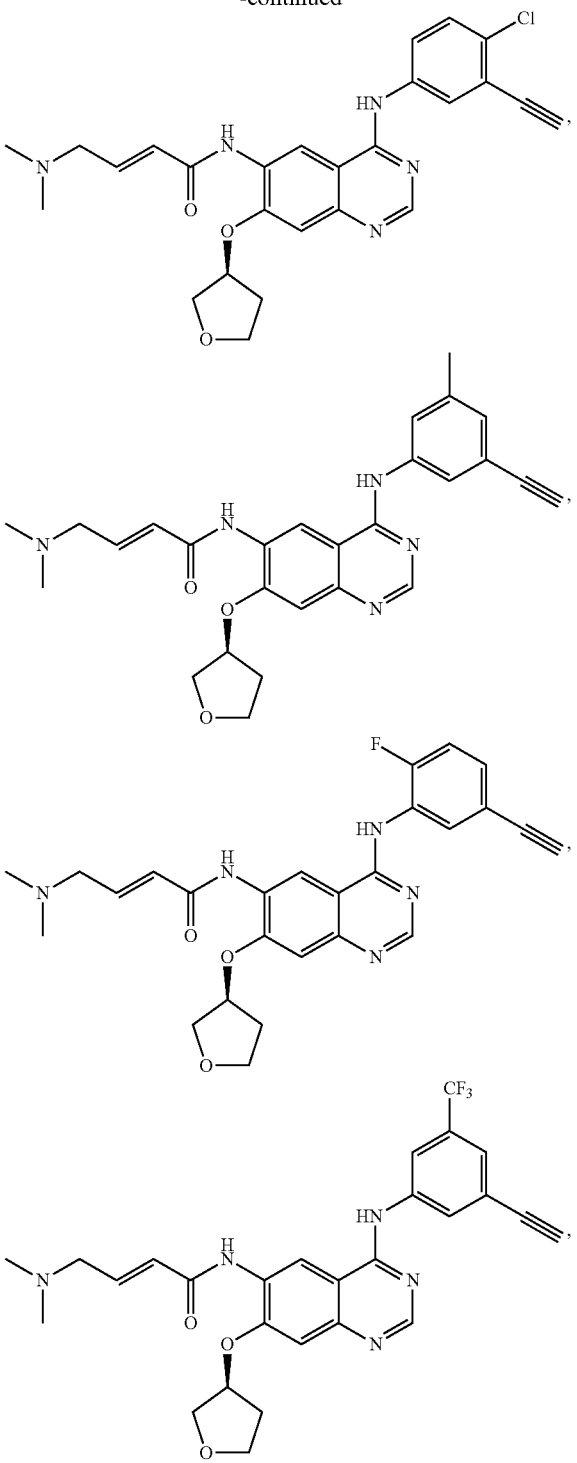

and the like, or a pharmaceutically acceptable salt, solvate, or a prodrug, or a metabolite thereof. In some embodiments, the selected compound is in the form of pharmaceutically acceptable salt. In some embodiments, the selected compound is in the form of a solvate. In other embodiments, the selected compound is in the form of a metabolite. In some embodiments, the selected compound is in the form of stereoisomer. In other embodiments, the selected compound is a tautomer. In other embodiments, the selected compound is in the form of a prodrug. In another embodiment, the deuterium enrichment in the selected compounds is at least about 1%.

In the preferred embodiments, the present invention provides (RS,E)-4-(diethylamino)-N-(4-((3-ethynylphenyl)amino)-7-((tetrahydrofuran-3-yl)oxy)quinazolin-6-yl)but-2-enamide, (S,E)-4-(diethylamino)-N-(4-((3-ethynylphenyl)amino)-7-((tetrahydrofuran-3-yl)oxy)quinazolin-6-yl)but-2-enamide; or (R,E)-4-(diethylamino)-N-(4-((3-ethynylphenyl)amino)-7-((tetrahydrofuran-3-yl)oxy)quinazolin-6-yl)but-2-enamide.

In some embodiments, the present invention provides pharmaceutical compositions comprising a compound of Formula I and a pharmaceutically acceptable carrier. In certain embodiments, the compositions are for the treatment of a disease regulated by a protein kinase. In certain embodiments, the compositions are for the treatment of a hyper-proliferative disorder. In other embodiments, the pharmaceutical compositions are suitable for oral, parenteral, or intravenous administration.

In some embodiments, the compound(s) of Formula I are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

In some embodiments, the present invention provides methods for regulating the kinase signaling transduction comprising administrating to a mammalian subject a therapeutically effective amount of a compound of Formula I.

In other embodiments provide herein methods for treating or preventing a HER kinases (including all mutant kinases) mediated disorder, said method comprises administrating to a mammalian subject a therapeutically effective amount of a compound of Formula I.

In yet another aspect, there are provided herein methods for inhibiting EGFR kinases, said method comprises administrating to a mammalian subject a therapeutically effective amount of a compound of Formula I.

In other embodiments provide herein methods for treating neoplasia comprising administrating to a mammalian subject in need thereof, a therapeutically effective amount of a compound of Formula I. In certain embodiments, the neoplasia is selected from liver cancer, skin cancer, leukemia, colon carcinoma, renal cell carcinoma, gastrointestinal stromal cancer, solid tumor cancer, myeloma, breast cancer, pancreatic carcinoma, non-small cell lung cancer, non-hodgkin's lymphoma, hepatocellular carcinoma, thyroid cancer, bladder cancer, colorectal cancer, and prostate cancer. In certain embodiments, the neoplasia is skin cancer. In some embodiments, the methods further comprise administering one or more anti-cancer agents.

In other embodiments, there are provided methods for treating or preventing a hyper-proliferative comprising administrating to a mammalian subject a therapeutically effective amount of a compound of Formula I.

The following definitions should assist in understanding the invention described herein.

The term "alkyl" is intended to include linear, branched, cyclic hydrocarbon group, which may be unsubstituted or optionally substituted with one or more functional groups. $C_1$-$C_3$ alkyl is intended to include $C_1$, $C_2$ and $C_3$ alkyl groups. Examples of alkyl include, but not limited to, methyl, ethyl, n-propyl, isopropyl, cyclopropyl. Alkyl may be substituted or unsubstituted. Illustrative substituted alkyl group include, but are not limited to, fluoromethyl, difluoromethyl, trifluoromethyl, hydoxymethyl, methoxymethyl, 2-fluoroethyl, 2-methoxyethyl, etc.

Halogen means fluorine, chlorine, bromine, and iodine.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as Deuterium and carbon such as $^{13}$C. Certain isotopically-labeled compounds of the invention, for example, those incorporating a radioactive isotope, are useful in drug and/or substrate tissue distribution studies. Substitution with heavier isotopes such as deuterium may afford certain therapeutic advantages resulting from greater metabolic stability; for example, increased in vivo half-life or reduced dosage requirements, and hence may be preferred in some circumstances. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "comprising" is meant to be open-ended, including the indicated component(s), but not excluding other elements.

The term "pharmaceutically acceptable" when used with reference to a compound of Formula I is intended to refer to a form of the compound that is safe for administration to a subject. For example, a free base, a salt form, a solvate, a hydrate, a prodrug or derivative form of a compound of Formula I, which has been approved for mammalian use, via oral ingestion or any other route of administration, by a governing authority or regulatory agency, such as the Food and Drug Administration (FDA) of the United States, is pharmaceutically acceptable.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "metabolite" as used herein means a physiologically active compound resulting from the metabolism of an inventive compound, when such compound is administered to a mammal. Metabolites of a compound may be identified using routine techniques known in the art.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I. A "pharmaceutically-acceptable prodrug" as used herein, denotes a prodrug, which is pharmaceutically acceptable.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Indication

The present invention provides compounds which are capable of modulating one or more signal transduction pathways comprising, but not limited to EGFR and/or ErbB2.

By the term "modulating," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effects. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

As stated hereinbefore, the compounds defined in the present invention possess biological activity. These properties may be assessed, for example, using one or more of the procedures set out below.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

In some embodiments, methods for treatment of androgen receptor-dependent or androgen receptor-mediated conditions or diseases, such as proliferative disorders, including cancer, comprises administration to a mammal a compound of Formula I in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

Specifically, the administration of compounds of the present invention in some embodiments are in conjunction with additional therapies known to those skilled in the art in the prevention or treatment of cancer. The foregoing description is merely illustrative of the invention and is not intended to limit the invention to the disclosed compounds, compositions and methods.

Synthesis of Compounds

The compounds of Formula I were synthesized according to the procedures described in the following Schemes to those skilled in the art, wherein the substituents are as defined for Formula I above, except where further noted. The synthetic methods described below are merely exemplary, and the compounds of the invention may also be synthesized by alternate routes as appreciated by persons of ordinary skill in the art.

The synthesis of compound 7 was conducted by reaction as described in Scheme 1. A few synthetic methods that can lead to the preparation of compounds of Formula I have been reported in the literature (US20050250761, U.S. Ser. No. 07/019,012, or US20100240649).

The reaction of commercial available or literature known starting materials compounds 1 and 2 in alcohol such as isopropyl alcohol led to the synthesis of compound 3. The replacement of fluoride in compound 3 with Tetrahydrofuran-3-ol sodium salt with heat gave compound 4. The nitro group of compound 4 was selectively reduced to the amino group with metal such as Fe, Zinc or $SnCl_2$ etc to generate compound 5. (Tetrahedron, 64(44), 10195-10200, 2008; Tetrahedron Letters, 42(46), 8141-8142; 2001; Faming Zhuanli Shenqing Gongkai Shuomingshu, 1313274, 19 Sep. 2001). The synthesis of compound 6 has been reported in the literature and reaction of compound 5 and 6 in solvent such as DMF afforded compound 7.

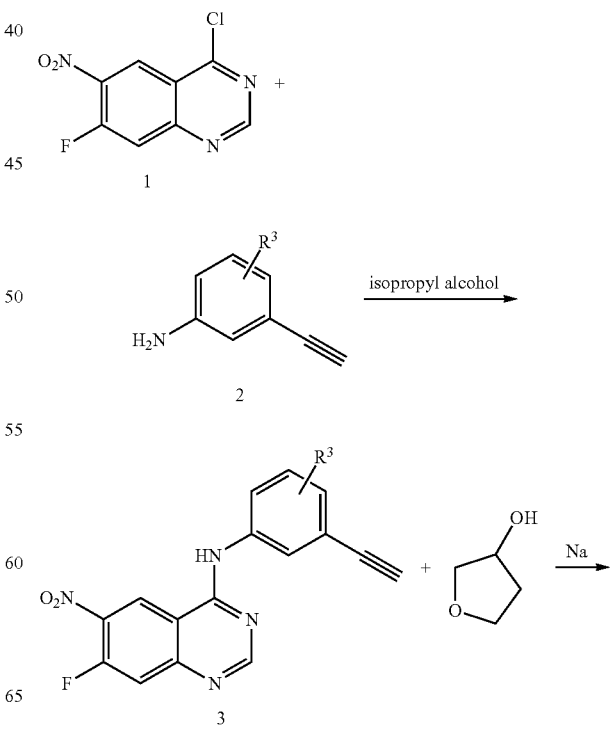

Scheme 1

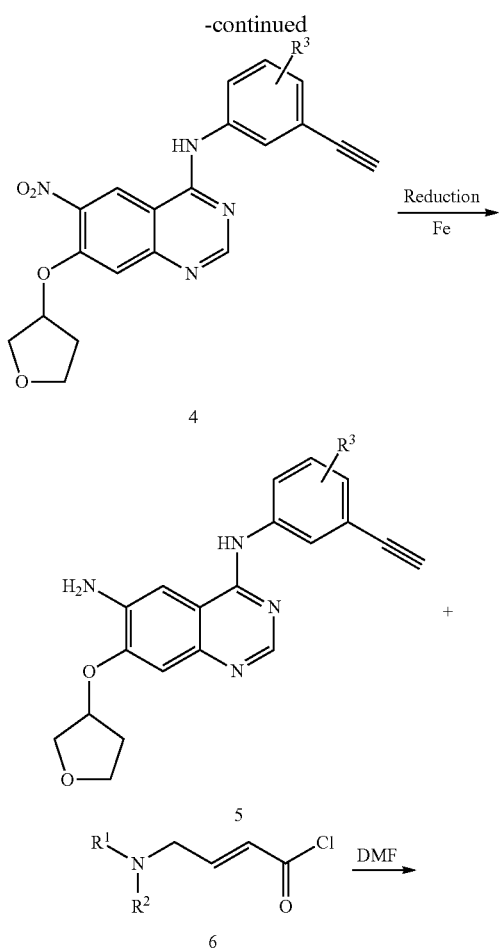

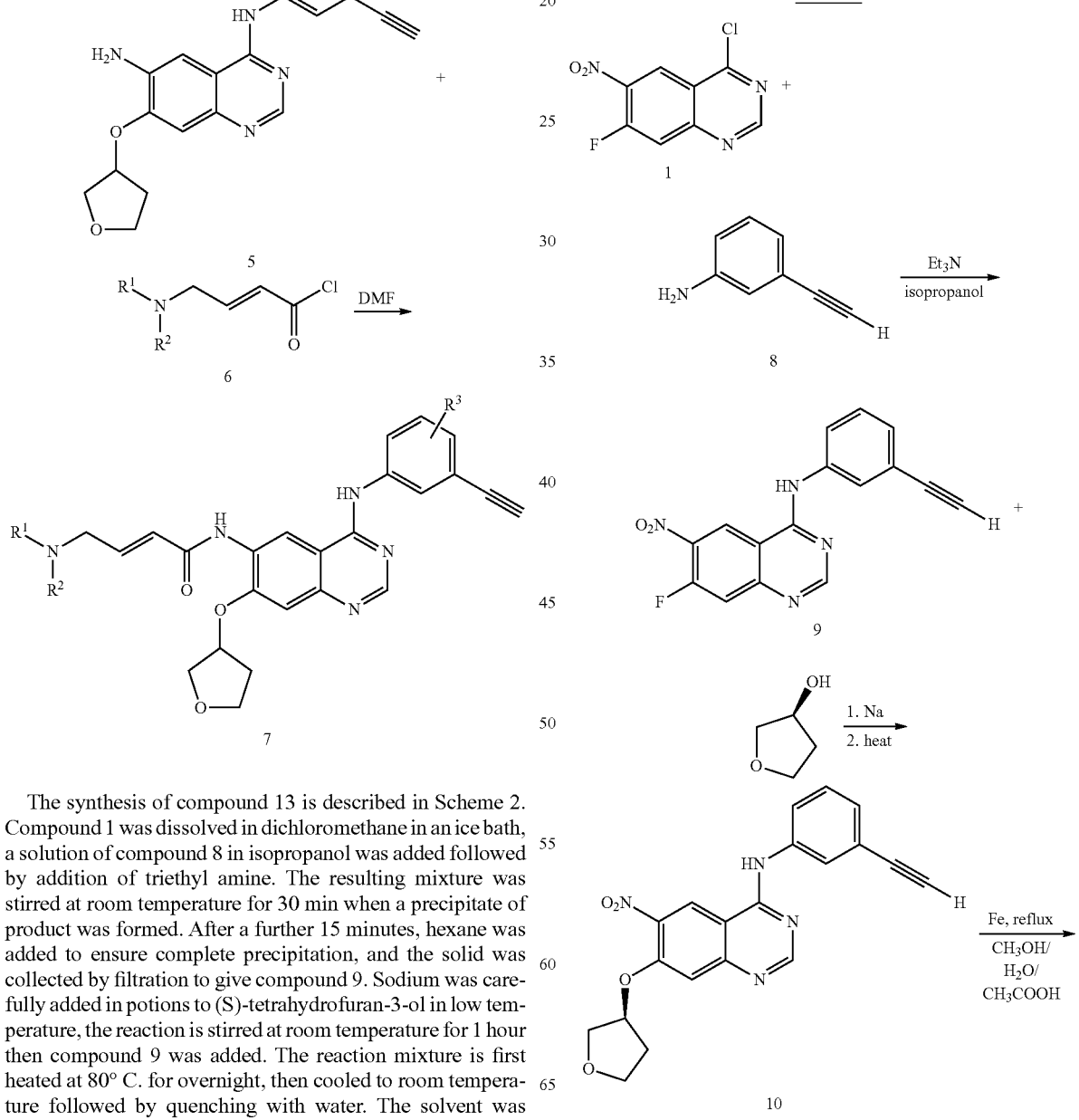

compound 10. A solution of compound 10 in methanol, water and acetic acid was heated for reflux followed by addition of Iron in batches. The reaction was refluxed for another 4 hours and cooled to room temperature. Work up and purification by flash chromatography using $CH_2Cl_2$ and methanol afforded compound 11. To a solution of compound 12 in dichloromethane was added oxalyl chloride and several drops of DMF. The reaction was stirred at room temperature for 1-2 hours and all the solvent was removed. The resulting residue was dissolved in THF and cooled to 0° C. and a mixture of compound 11 and triethyl amine were added. The reaction was stirred at 40° C. for 1-2 hours, water was added and all the solvent was removed under vacuum. The product was extracted with dichloromethane, dried over with $MgSO_4$, filtered and concentrated. Purification by flash chromatography afforded compound 13.

The synthesis of compound 13 is described in Scheme 2. Compound 1 was dissolved in dichloromethane in an ice bath, a solution of compound 8 in isopropanol was added followed by addition of triethyl amine. The resulting mixture was stirred at room temperature for 30 min when a precipitate of product was formed. After a further 15 minutes, hexane was added to ensure complete precipitation, and the solid was collected by filtration to give compound 9. Sodium was carefully added in potions to (S)-tetrahydrofuran-3-ol in low temperature, the reaction is stirred at room temperature for 1 hour then compound 9 was added. The reaction mixture is first heated at 80° C. for overnight, then cooled to room temperature followed by quenching with water. The solvent was removed under vacuum and the solid was filtered to afford

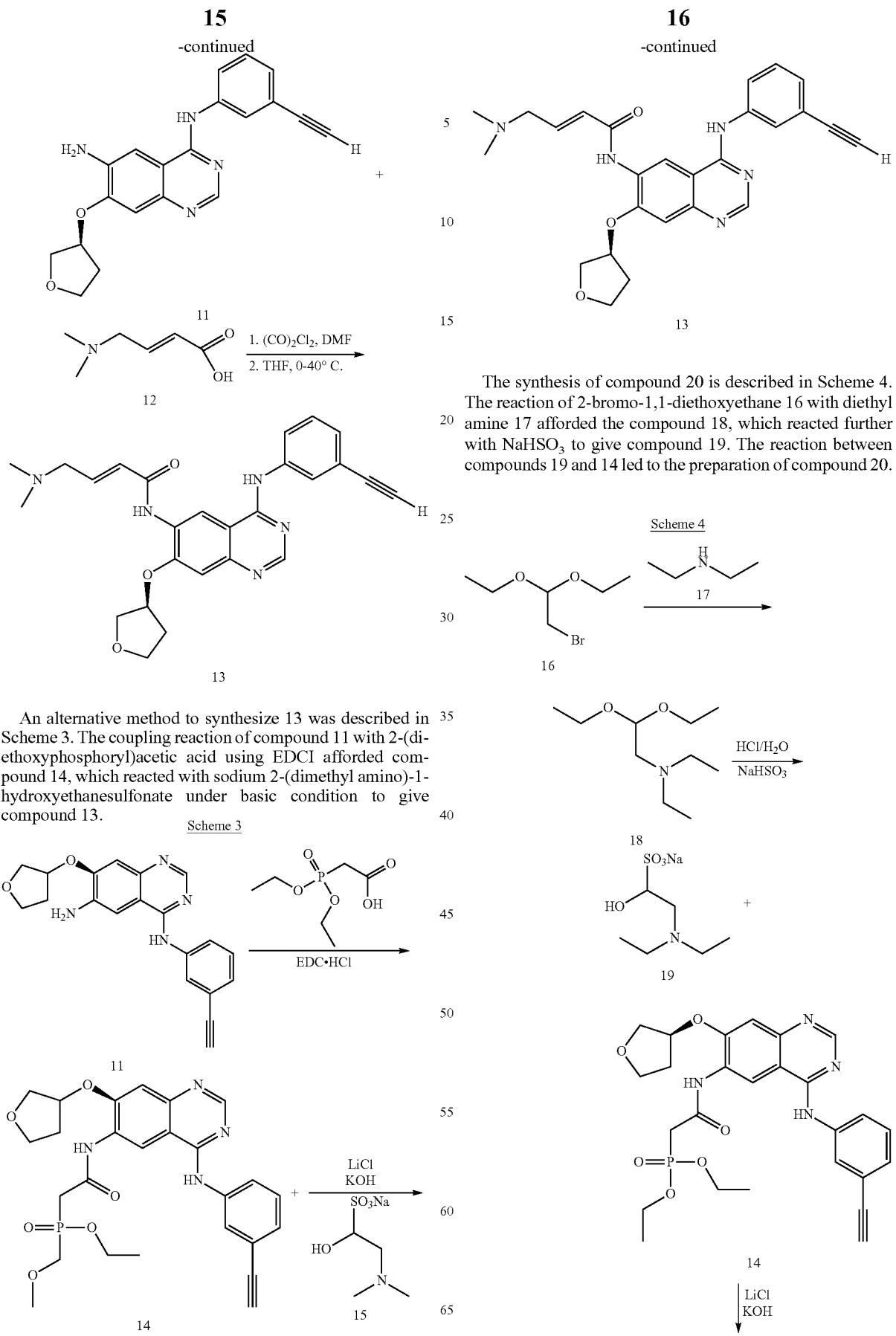

The synthesis of compound 20 is described in Scheme 4. The reaction of 2-bromo-1,1-diethoxyethane 16 with diethyl amine 17 afforded the compound 18, which reacted further with NaHSO$_3$ to give compound 19. The reaction between compounds 19 and 14 led to the preparation of compound 20.

An alternative method to synthesize 13 was described in Scheme 3. The coupling reaction of compound 11 with 2-(diethoxyphosphoryl)acetic acid using EDCI afforded compound 14, which reacted with sodium 2-(dimethyl amino)-1-hydroxyethanesulfonate under basic condition to give compound 13.

-continued

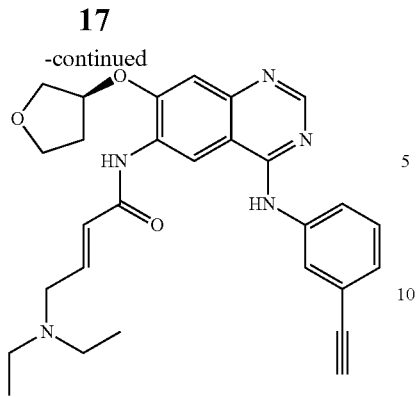

DESCRIPTION OF EMBODIMENTS

These detailed descriptions are presented for illustrative purposes only and are not intended as a restriction on the scope of the invention.

Proton NMR Spectra

Unless otherwise indicated, all $^1$H NMR spectra were run on a Varian series Mercury 300, 400 MHz instrument or a Bruker series 400 MHz instrument. Where so characterized, all observed protons are reported as parts-per-million (ppm) downfield from tetramethylsilane (TMS) or other internal reference in the appropriate solvent indicated.

ABBREVIATION

DMF means N,N-dimethylformamide.
DCM means dichloromethane.
DIPEA means diisopropyl ethylamine.
THF means tetrahydrofuran.
TEA means triethylamine.
EA means ethyl acetate.
EDC means 1-ethyl-3-(3-dimethylaminopropyl)carbodiimide.
AST means aspartate aminotransferase.
ALT means alanine aminotransferase.
KI means Potassium Iodine.

Example 1

Preparation of 4-chloro-7-fluoro-6-nitroquinazoline (Compound 1)

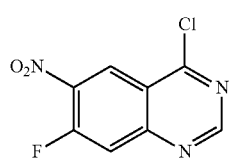 [SMILES: O=[N+]([O-])c1cc2c(Cl)ncnc2cc1F]

7-fluoro-6-nitroquinazolin-4-ol (15 g, 0.072 mol) was added into 150 mL SOCl$_2$ and 10 drops of DMF was added. The solution was heated to reflux for 4 hours, then SOCl$_2$ was removed under reduce pressure to give 4-chloro-7-fluoro-6-nitro quinazoline as a yellow powder 15.4 g (94.4% yield).

Example 2

Preparation of N-(3-ethynylphenyl)-7-fluoro-6-nitro-quinazolin-4-amine (Compound 9)

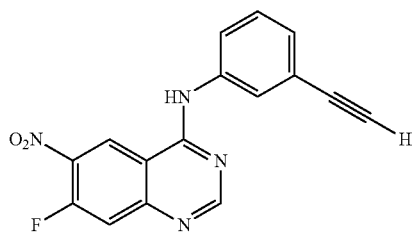 [SMILES: C#Cc1cccc(Nc2ncnc3cc(F)c([N+](=O)[O-])cc23)c1]

To a solution of 4-chloro-7-fluoro-6-nitroquinazoline (12 g, 0.052 mol) in 120 mL DCM in an ice bath was added slowly a solution of 3-ethynylaniline (7 g, 0.060 mol) in 200 mL isopropanol. The reaction solution was stirred for 1 hour, then TEA (7 g, 0.069 mol) was added and stirred for another 0.5 hour at room temperature. The resulting solid precipitate was filtered and washed with 20 mL isopropanol twice, 20 mL H$_2$O for twice, and dried to give N-(3-ethynylphenyl)-7-fluoro-6-nitroquinazolin-4-amine as yellow solid 8.2 g (50.3% yield).

Example 3

Preparation of (S)—N-(3-ethynylphenyl)-6-nitro-7-((tetrahydrofuran-3-yl)oxy)quinazolin-4-amine (Compound 10)

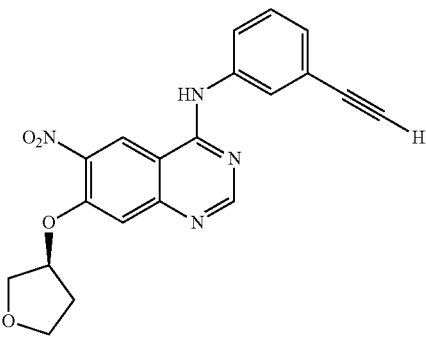 [SMILES: C#Cc1cccc(Nc2ncnc3cc(O[C@H]4CCOC4)c([N+](=O)[O-])cc23)c1]

In an ice bath, NaH (1.87 g, 60%, 0.046 mol) was carefully added into a solution of (S)-tetrahydrofuran-3-ol (3.43 g, 0.039 mmol) in 100 mL anhydrous THF, and stirred for 2 hours at room temperature. Then N-(3-ethynylphenyl)-7-fluoro-6-nitroquinazolin-4-amine (10 g, 0.032 mol) was added and stirred for at 60° C. overnight. The solution was quenched with 1 mL H$_2$O and concentrated, the residue was purified by silica gel column to give (S)—N-(3-ethynylphenyl)-6-nitro-7-(tetrahydrofuran-3-yloxy)quinazolin-4-amine as yellow solid 7.1 g (58.1% yield).

Example 4

Preparation of (S)—N⁴-(3-ethynylphenyl)-7-((tetrahydrofuran-3-yl)oxy)quinazoline-4,6-diamine (Compound 11)

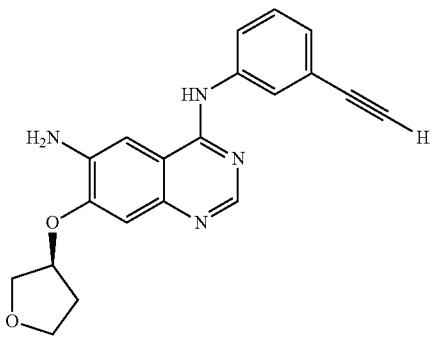 [SMILES: C#Cc1cccc(Nc2ncnc3cc(O[C@H]4CCOC4)c(N)cc23)c1]

(S)—N-(3-ethynylphenyl)-6-nitro-7-(tetrahydrofuran-3-yloxy)quinazolin-4-amine (4 g, 0.011 mol) and ammonia hydrochloride (2.4 g, 0.045 mol) was mixed in a solution of 150 mL methanol, 75 mL H₂O, 50 ml EA, and then was heated to 70° C. Fe (4.8 g, 0.085 mol) was added and the reaction mixture was heated to reflux for 4 hours. The resulting reaction solution was filtered and concentrated under reduced pressure to remove most of solvent. The residue was diluted in 100 mL H₂O, extracted with ethyl acetate (3×100 mL), the organic layers were concentrated to give (S)—N⁴-(3-ethynylphenyl)-7-(tetrahydrofuran-3-yloxy)quinazoline-4,6-diamine as grey solid 1.8 g (48.9% yield).

Example 5

Preparation of (S,E)-4-(dimethylamino)-N-(4-((3-ethynylphenyl)amino)-7-((tetrahydrofuran-3-yl)oxy)quinazolin-6-yl)but-2-enamide (Compound 13)

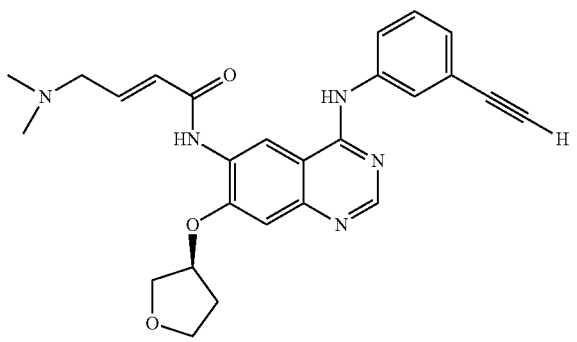 [SMILES: C#Cc1cccc(Nc2ncnc3cc(O[C@H]4CCOC4)c(NC(=O)/C=C/CN(C)C)cc23)c1]

Step 1: (S)—N⁴-(3-ethynylphenyl)-7-(tetrahydrofuran-3-yloxy)quinazoline-4,6-diamine (1.4 g, 4.0 mmol), 2-(diethoxyphosphoryl)acetic acid (0.92 g, 4.7 mmol) and EDC.HCl (1.5 g, 7.7 mmol) were added into 15 mL DMF, and then DIPEA (1.0 g, 7.7 mmol) was added and stirred for 4 hours at 50 degree. The reaction solution was poured into 200 mL ethyl acetate and washed with 3×100 mL H₂O. The organic layers were concentrated and applied on a silica gel column to afford (S)-diethyl 2-(4-(3-ethynylphenylamino)-7-(tetrahydrofuran-3-yloxy)quinazolin-6-ylamino)-2-oxoethylphosphonate (Compound 14) as off-white solid 1.2 g (57.1% yield).

Step 2. (S)-diethyl 2-(4-(3-ethynylphenylamino)-7-(tetrahydrofuran-3-yloxy)quinazolin-6-ylamino)-2-oxo ethylphosphonate (1 g, 1.9 mmol) and LiCl (90 mg, 2.1 mmol) were added into 18 mL methanol, then aqueous KOH (40%) (2.2 g) was added at 0° C. Then sodium 2-(dimethyl amino)-1-hydroxyethanesulfonate (0.73 g, 3.81 mmol) in 20 mL H₂O was added. The resulting solution was stirred for 2 hours at 50 degree. The reaction solution was poured into 200 mL EA and 200 mL H₂O, the organic layer was concentrated and applied on a silica gel column to afford (S,E)-4-(dimethylamino)-N-(4-((3-ethynylphenyl)amino)-7-((tetrahydrofuran-3-yl)oxy)quinazolin-6-yl)but-2-enamide as white solid 220 mg (24.4% yield). ¹H-NMR (DMSO-d⁶): δ2.12-2.16 (m, 1H), 2.18 (s, 6H), 2.30-2.39 (m, 1H), 3.09 (d, J=5.6 Hz, 2H), 3.75-3.82 (m, 1H), 3.91-3.98 (m, 1H), 3.99-4.03 (m, 2H), 4.19 (s, 1H), 5.29-5.30 (m, 1H), 6.59 (d, J=15.6 Hz, 1H), 6.77-6.89 (m, 1H), 7.19-7.23 (m, 2H), 735-7.42 (m, 1H), 7.85-7.89 (m, 1H), 8.01 (s, 1H), 8.52 (s, 1H), 8.96 (s, 1H), 9.49 (s, 1H), 9.78 (s, 1H). MS m/z 458 [M+1].

Example 6

Preparation of 2,2-diethoxy-N,N-diethylethanamine (Compound 18)

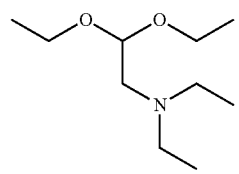

2-bromo-1,1-diethoxyethane (10 g, 0.051 mol), diethylamine (11 g, 0.15 mol) and KI (8.5 g, 0.051 mol) were added in 100 mL acetone, and stirred for overnight at 40 degree. The resulting solution was filtered, concentrated and purified with silica gel column to give 2,2-diethoxy-N,N-diethylethanamine as brown oil 2.0 g (20.8% yield).

Example 7

Preparation of sodium 2-(diethylamino)-1-hydroxyethanesulfonate (Compound 19)

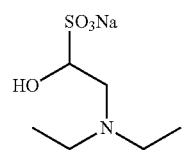

2,2-diethoxy-N,N-diethylethanamine (140 mg, 0.75 mmol) was added in 0.1 mL H₂O. Concentrated HCl (190 mg) was added dropwise in an ice bath. The solution was stirred for 2 hours at 40 degree. NaHSO₃ (350 mg, 3.36 mmol) in 0.6 mL H₂O was added to the reaction solution in an ice bath and stirred for 1 hour at room temperature, then 0.6 ml ethanol was added and stirred for 1 hour at room temperature. This reaction solution was concentrated, the resulting residue was used directly for the next step.

Example 8

Preparation of (S,E)-4-(diethylamino)-N-(4-((3-ethynylphenyl)amino)-7-((tetrahydrofuran-3-yl)oxy)quinazolin-6-yl)but-2-enamide (Compound 20)

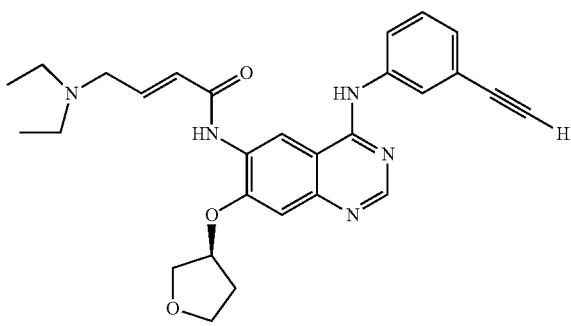 [SMILES: C#Cc1cccc(Nc2ncnc3cc(O[C@H]4CCOC4)c(NC(=O)/C=C/CN(CC)CC)cc23)c1]

(S)-diethyl 2-(4-(3-ethynylphenylamino)-7-(tetrahydrofuran-3-yloxy)quinazolin-6-ylamino)-2-oxo ethylphosphonate (100 mg, 0.19 mmol) and LiCl (10 mg, 0.21 mmol) were added into 1 mL methanol, then aqueous KOH (40%) (400 mg) was added at 0° C. The reaction was added sodium 2-(diethylamino)-1-hydroxyethanesulfonate (70 mg) in 1 mL $H_2O$. The resulting solution was stirred for 2 hours at 50 degree. The reaction solution was poured into a mixture of 20 ml EA and 20 mL $H_2O$. The organic layer was concentrated, purified by flash column chromatography in silica gel to give (S,E)-4-(diethylamino)-N-(4-((3-ethynylphenyl)amino)-7-((tetrahydrofuran-3-yl)oxy)quinazolin-6-yl)but-2-enamide as off-white solid 12 mg (12.5% yield). $^1$H-NMR (CDCl$_3$, 400 MHz): δ 9.17 (1H, s), 8.67 (1H, s), 8.05 (1H, s), 7.96 (1H, s), 7.78-7.76 (1H, m), 7.60 (1H, s), 7.37-7.34 (1H, m), 7.29 (1H, s), 7.20 (1H, s), 7.12-7.07 (1H, m), 6.22 (1H, d, J=15.2 Hz), 5.19-5.16 (1H, m), 4.11-4.07 (1H, m), 4.05-4.04 (2H, m), 3.98-3.92 (1H, m), 3.34-3.32 (2H, m), 3.10 (1H, s), δ2.59 (4H, q, J=7.2 Hz), 2.45-2.41 (1H, m), 2.29-2.25 (1H, m), 1.08 (6H, t, J=7.2 Hz). MS m/z 487 [M+1].

Biological Assays:

An In Vitro Assay which Determines the Ability of a Test Compound to Inhibit EGFR (T790M/L858R) Kinase Activity.

1. Materials: EGFR(T790M/L858R) (BPS#40350, Lot#101214, 25 ng/Reaction); Poly (Glu, Tyr) sodium salt, (4:1, Glu:Tyr) (Sigma#P7244) Kinase-Glo Plus Luminescence; kinase assay kit (Promega#V3772); Substrates, 0.2 mg/ml poly(Glu, Tyr); ATP, 10 μM; Compounds test range, 0.1 nM-3 μM.

2. The assay was performed using Kinase-Glo Plus luminescence kinase assay kit (Promega). It measures kinase activity by quantitating the amount of ATP remaining in solution following a kinase reaction. The luminescent signal from the assay is correlated with the amount of ATP present and is inversely correlated with the amount of kinase activity. The compounds were diluted in 10% DMSO and 50 of the dilution was added to a 50 μl reaction so that the final concentration of DMSO is 1% in all of reactions. All of the enzymatic reactions were conducted at 30° C. for 25 minutes. The 50 μl reaction mixture contains 40 mM Tris, pH 7.4, 10 mM MgCl$_2$, 0.1 mg/ml BSA, 1 mM DTT, 0.2 mg/ml Poly (Glu, Tyr) substrate, 10 μM ATP and EGFR (Table 2.3.1). After the enzymatic reaction, 50 μl of Kinase-Glo Plus Luminescence kinase assay solution (Promega) was added to each reaction and incubate the plate for 5 minutes at room temperature. Luminescence signal was measured using a BioTek Synergy 2 microplate reader.

3. EGFR activity assays were performed in duplicate at each concentration. The luminescence data were analyzed using the computer software, Graphpad Prism. The difference between luminescence intensities in the absence of EGFR ($Lu_t$) and in the presence of EGFR ($Lu_c$) was defined as 100% activity ($Lu_t$-$Lu_c$). Using luminescence signal (Lu) in the presence of the compound, % activity was calculated as: % activity={($Lu_t$-Lu)/($Lu_t$-$Lu_c$)}×100%, where Lu=the luminescence intensity in the presence of the compound (all percent activities below zero were shown zero in the table). The values of % activity versus a series of compound concentrations were then plotted using non-linear regression analysis of Sigmoidal dose-response curve generated with the equation $Y=B+(T-B)/1+10^{((LogEC50-X)\times Hill\ Slope)}$, where Y=percent activity, B=minimum percent activity, T=maximum percent activity, X=logarithm of compound and Hill Slope=slope factor or Hill coefficient. The IC50 value was determined by the concentration causing a half-maximal percent activity.

Enzyme assay (EGFR/T790M): Compounds 20 and compound 13 were both found to have potency ($IC_{50}$)<100 nM.

A Representative Number of Compounds were Assayed Against Different Cancer Cell Lines Such as A431, BT474, NCI—H1975, SK—OV-3, SK—Br-3 and A549 Using the Cell Proliferation Assays:

1. 5×10$^3$ cells per well in 100 μl of medium were seeded in 96-well plate, here the medium contained 5% FBS 2. 24 hours later, 100 μl fresh medium was added with various concentrations of compounds into each well, while the medium here was free of FBS.

3. After the cells were treated with compounds for 72 hours, 20 μl MTT (5 mg/ml) was added into each well, and then the assay plate was incubated at 37° C. for 4 more hours.

4. The assay plate was centrifuged at 800 g for 10 min. The medium was aspirated, 150 μl DMSO was added into each well. The plate was gently shaken for 10 min.

5. The absorbance at 570 nm was measured on the plate reader.

6. IR %=(WC−WT)/WC×100%.

The following Table 1 lists compounds representative of the invention and their activity in cell assays.

TABLE 1

|  | Afatinib | Compound 13 | Compound 20 |
| --- | --- | --- | --- |
| A431 | NA | 3.099 uM | 1.791 uM |
| BT474 | 47 nM | 57 nM | 6.8 nM |

Compounds 20 and compound 13 were both found to have potency ($IC_{50}$)<10 uM over NCI—H1975, SK—OV-3, SK—Br-3 and A549 cell assays.

In Vivo Xenograft Assay:

A representative protocol for the in vivo experiment is as followed to establish the subcutaneous NCI—H1975 cell line xenograft model in nude mice and to evaluate the in vivo therapeutic efficacy of the compounds: H1975 cells were cultured in RPMI1640 containing 10% fetal bovine serum, 1% L-glutamine, 100 U/mL penicillinG and 100 μg/mL streptomycin. Cells in logarithmic growth phase were harvested and resuspended in 1×PBS for implantation.

Tumor xenografts were established by injecting tumor cells 5×10⁶/mouse into the right flank by sc under sterile conditions. When the tumors reached an appropriate size (100-200 mm³), mice were randomized into 6 mice per group (8 mice in control group). The tumors were measured using a caliper in two dimensions, length (a), and width (b). Tumor volumes were estimated from measurements of two diameters of the individual tumors as follows:

$$\text{Tumor Volume(mm}^3\text{)}=(a \times b^2)/2$$

The tumor sizes and animal body weights were measured twice a week. Mice were observed daily for clinical signs. Blood samples were collected 2 hours after last treatment, plasma samples were prepared and stored at −80° C. Tumor tissues were separated, weighed, taken picture, and subsequently stored at −80° C. for further analysis. All animal experiments were performed in accordance with the Guidelines for Use and Care of Animals of the University of Traditional Medicine. The parameters for in vivo efficacy evaluation were calculated according to the guidance of SFDA. Percent T/C (%) was calculated with the following formula: T/C (%)=($T_{RTV}$/$C_{RTV}$)×100%, where $T_{RTV}$ and $C_{RTV}$ stand for relative tumor volume in treatment group and vehicle control group, respectively. Relative tumor volume (RTV) was calculated using the formula: RTV=$V_t$/$V_0$, where $V_t$ represents volume on testing day, and $V_0$ represents volume on first day of treatment. Tumor growth inhibition (TGI, %) were calculated as TGI (%)=(Ctw−Ttw)/Ctw×100%, where Ctw and Ttw represent mean tumor weight in vehicle control and treatment group, respectively.

At study endpoint, after blood collection, mice were practiced euthanasia by cervical dislocation, the tumor tissue was collected first, then abdominal cavity was cut open, liver and spleen were excised, then weight after the gallbladder was removed respectively Organ weight between the treated versus the control groups were compared. Compound 20 and compound 13 showed good efficacy in the NCI—H1975 xenograft study.

At equal dose of 15 mg/kg, Compound 20 has much smaller body weight loss than compound 13 or Afatinib (Table 2).

TABLE 2

In vivo NCI-H1975 xenograft study body weight change

| | Control | Afatinib (15 mg/kg) | Compound 13 (15 mg/kg) | Compound 20 (15 mg/kg) |
|---|---|---|---|---|
| Day 7 Weight change | 5.9% | −0.9% | 0.1% | 3.5% |

At equal dose of 15 mg/kg, compound 20 has much less increased aspartate aminotransferase (AST) level than Afatinib (Table 3).

TABLE 3

In vivo NCI-H1975 AST and ALT change

| | Control | Afatinib (15 mg/kg) | Compound 20 (15 mg/kg) |
|---|---|---|---|
| AST | 165.88 | 265.67 | 142.33 |
| ALT | 38.75 | 49.50 | 41.67 |

A representative protocol for the in vivo experiment to establish the subcutaneous A431 cell line xenograft model in nude mice and to evaluate the in vivo therapeutic efficacy of the compounds is similar to the protocol described for subcutaneous NCI—H1975 cell line xenograft model in nude mice. Compound 20 were dosed at 10 mg/kg by oral gavage once daily for 14 days. Tumor growth inhibition (TGI, %) was calculated. Compound 20 showed significant tumor growth inhibition, TGI=94%.

At equal dose of 10 mg/kg, Compound 20 has much smaller body weight loss than Afatinib (Table 4).

TABLE 4

In vivo A431 xenograft body weight change

| | Control | Afatinib (10 mg/kg) Body weight change | Compound 20 (10 mg/kg) Body weight change |
|---|---|---|---|
| Day 7 | 3.8% | −2.2% | 1.5% |
| Day 10 | 4.8% | 0.4% | 4.3% |

Solubility Measurement:

Preparation of reference standard solution: 9.45 mg of Compound 13 or 9.22 mg of Compound 20 was added individually to 100 mL volumetric flask each. The compound was diluted with acetonitrile to 100 mL.

Preparation of sample solution: 5.26 mg of Compound 13 or 6.24 mg of Compound 20 was added individually to 2 mL eppendorf tube (EP), followed by addition of 1 mL of pH 6.8 buffer solution (20 mM). The solution was shook for 2 minutes and left for 30 minutes at 25° C. After standing for 30 minutes, precipitate was formed in the bottom of the EP. The solutions was filtered through 0.2 um membrane filter, and then diluted by 50 times with water.

The standard and sample solutions were injected into the HPLC on a Shim-Pack CLC-ODS $C_{18}$ column (150 mm×6.0 mm, 5 um) with the same volume. The mobile phase consisted of acetonitrile with 2% trichloromethane −20 mM $KH_2PO_4$ buffer (pH=6.8) at a flow rate of 1 mL/minutes (40:60). The detection wavelength is at 264 nm. Calculation: solubility of sample=the concentration of standard×Area of sample×50/Area of standard. Compound 20 has higher solubility than compound 13.

Solubility of Compounds of the Invention

| | Compound 13 | Compound 20 |
|---|---|---|
| Solubility at pH 6.8 | 0.150 mg/mL | 3.373 mg/mL |
| Solubility at pH 7.6 | 0.025 mg/mL | 0.238 mg/mL |

The invention claimed is:
1. A compound of Formula I:

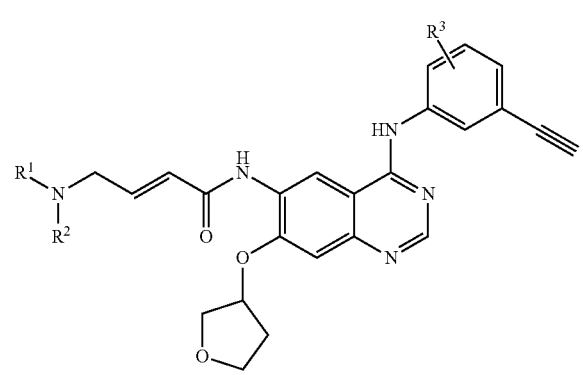

or a pharmaceutically acceptable salt, solvate, stereoisomer or tautomer thereof, wherein R¹ and R² are independently selected from hydrogen, and C₁-C₃ alkyl; and R³ is selected from hydrogen, halogen, CN, and CF₃.

2. The compound of claim 1 or a pharmaceutically acceptable salt thereof, wherein
R¹ and R² are independently selected from the group consisting of methyl and ethyl; and
R³ is selected from the group consisting of hydrogen, Cl, and F.

3. The compound of claim 1 or a pharmaceutically acceptable salt thereof, wherein
R¹ and R² are both ethyl; and
R³ is selected from the group consisting of hydrogen, Cl, and F.

4. The compound of claim 1 or a pharmaceutically acceptable salt thereof, wherein
R¹ and R² are both ethyl; and
R³ is selected from the group consisting of hydrogen and CF₃.

5. The compound of claim 1 or a pharmaceutically acceptable salt thereof, wherein said compound is selected from the group consisting of:

(RS,E)-4-(dimethylamino)-N-(4-((3-ethynylphenyl)amino)-7-((tetrahydrofuran-3-yl)oxy)quinazolin-6-yl)but-2-enamide;

(RS,E)-4-(diethylamino)-N-(4-((3-ethynylphenyl)amino)-7-((tetrahydrofuran-3-yl)oxy)quinazolin-6-yl)but-2-enamide;

(RS,E)-4-(dipropylamino)-N-(4-((3-ethynylphenyl)amino)-7-((tetrahydrofuran-3-yl)oxy)quinazolin-6-yl)but-2-enamide;

(RS,E)-4-(ethyl(methyl)amino)-N-(4-((3-ethynylphenyl)amino)-7-((tetrahydrofuran-3-yl)oxy)quinazolin-6-yl)but-2-enamide;

(RS,E)-4-(dimethylamino)-N-(4-((3-ethynyl-4-fluorophenyl)amino)-7-((tetrahydrofuran-3-yl)oxy)quinazolin-6-yl)but-2-enamide;

(RS,E)-N-(4-((4-chloro-3-ethynylphenyl)amino)-7-((tetrahydrofuran-3-yl)oxy)quinazolin-6-yl)-4-(dimethylamino)but-2-enamide;

(RS,E)-4-(dimethylamino)-N-(4-((5-ethynyl-2-fluorophenyl)amino)-7-((tetrahydrofuran-3-yl)oxy)quinazolin-6-yl)but-2-enamide;

(RS,E)-4-(dimethylamino)-N-(4-((3-ethynyl-5-(trifluoromethyl)phenyl)amino)-7-((tetrahydrofuran-3-yl)oxy)quinazolin-6-yl)but-2-enamide;

(S,E)-4-(dimethylamino)-N-(4-((3-ethynylphenyl)amino)-7-((tetrahydrofuran-3-yl)oxy)quinazolin-6-yl)but-2-enamide;

(R,E)-4-(dimethylamino)-N-(4-((3-ethynylphenyl)amino)-7-((tetrahydrofuran-3-yl)oxy)quinazolin-6-yl)but-2-enamide;

(S,E)-4-(diethylamino)-N-(4-((3-ethynylphenyl)amino)-7-((tetrahydrofuran-3-yl)oxy)quinazolin-6-yl)but-2-enamide;

(R,E)-4-(diethylamino)-N-(4-((3-ethynylphenyl)amino)-7-((tetrahydrofuran-3-yl)oxy)quinazolin-6-yl)but-2-enamide;

(S,E)-4-(dipropylamino)-N-(4-((3-ethynylphenyl)amino)-7-((tetrahydrofuran-3-yl)oxy)quinazolin-6-yl)but-2-enamide;

(R,E)-4-(dipropylamino)-N-(4-((3-ethynylphenyl)amino)-7-((tetrahydrofuran-3-yl)oxy)quinazolin-6-yl)but-2-enamide;

(S,E)-4-(ethyl(methyl)amino)-N-(4-((3-ethynylphenyl)amino)-7-((tetrahydrofuran-3-yl)oxy)quinazolin-6-yl)but-2-enamide;

(S,E)-4-(dimethylamino)-N-(4-((3-ethynyl-4-fluorophenyl)amino)-7-((tetrahydrofuran-3-yl)oxy)quinazolin-6-yl)but-2-enamide;

(S,E)-N-(4-((4-chloro-3-ethynylphenyl)amino)-7-((tetrahydrofuran-3-yl)oxy)quinazolin-6-yl)-4-(dimethylamino)but-2-enamide;

(S,E)-4-(dimethylamino)-N-(4-((5-ethynyl-2-fluorophenyl)amino)-7-((tetrahydrofuran-3-yl)oxy)quinazolin-6-yl)but-2-enamide;

(S,E)-4-(dimethylamino)-N-(4-((3-ethynyl-5-(trifluoromethyl)phenyl)amino)-7-((tetrahydrofuran-3-yl)oxy)quinazolin-6-yl)but-2-enamide;

(S,E)-4-(ethylamino)-N-(4-((3-ethynylphenyl)amino)-7-((tetrahydrofuran-3-yl)oxy)quinazolin-6-yl)but-2-enamide;

(S,E)-4-(diethylamino)-N-(4-((3-ethynyl-4-fluorophenyl)amino)-7-((tetrahydrofuran-3-yl)oxy)quinazolin-6-yl)but-2-enamide;

(S,E)-N-(4-((4-chloro-3-ethynylphenyl)amino)-7-((tetrahydrofuran-3-yl)oxy)quinazolin-6-yl)-4-(diethylamino)but-2-enamide;

(S,E)-N-(4-((4-cyano-3-ethynylphenyl)amino)-7-((tetrahydrofuran-3-yl)oxy)quinazolin-6-yl)-4-(diethylamino)but-2-enamide;

(S,E)-4-(diethylamino)-N-(4-((3-ethynyl-4-(trifluoromethyl)phenyl)amino)-7-((tetrahydrofuran-3-yl)oxy)quinazolin-6-yl)but-2-enamide;

(S,E)-4-(diethylamino)-N-(4-((3-ethynyl-5-fluorophenyl)amino)-7-((tetrahydrofuran-3-yl)oxy)quinazolin-6-yl)but-2-enamide;

(S,E)-N-(4-((3-chloro-5-ethynylphenyl)amino)-7-((tetrahydrofuran-3-yl)oxy)quinazolin-6-yl)-4-(diethylamino)but-2-enamide;

(S,E)-4-(diethylamino)-N-(4-((3-ethynyl-5-(trifluoromethyl)phenyl)amino)-7-((tetrahydrofuran-3-yl)oxy)quinazolin-6-yl)but-2-enamide;

(S,E)-N-(4-((3-cyano-5-ethynylphenyl)amino)-7-((tetrahydrofuran-3-yl)oxy)quinazolin-6-yl)-4-(diethylamino)but-2-enamide;

(S,E)-4-(ethylamino)-N-(4-((3-ethynyl-5-(trifluoromethyl)phenyl)amino)-7-((tetrahydrofuran-3-yl)oxy)quinazolin-6-yl)but-2-enamide;

(S,E)-4-(diethylamino)-N-(4-((5-ethynyl-2-fluorophenyl)amino)-7-((tetrahydrofuran-3-yl)oxy)quinazolin-6-yl)but-2-enamide;

(S,E)-N-(4-((2-chloro-5-ethynylphenyl)amino)-7-((tetrahydrofuran-3-yl)oxy)quinazolin-6-yl)-4-(diethylamino)but-2-enamide;

(S,E)-4-(diethylamino)-N-(4-((5-ethynyl-2-(trifluoromethyl)phenyl)amino)-7-((tetrahydrofuran-3-yl)oxy)quinazolin-6-yl)but-2-enamide;

(S,E)-N-(4-((2-cyano-5-ethynylphenyl)amino)-7-((tetrahydrofuran-3-yl)oxy)quinazolin-6-yl)-4-(diethylamino)but-2-enamide;

(S,E)-4-(diethylamino)-N-(4-((5-ethynyl-2,4-difluorophenyl)amino)-7-((tetrahydrofuran-3-yl)oxy)quinazolin-6-yl)but-2-enamide;

(S,E)-N-(4-((4-chloro-5-ethynyl-2-fluorophenyl)amino)-7-((tetrahydrofuran-3-yl)oxy)quinazolin-6-yl)-4-(ethylamino)but-2-enamide;

(S,E)-4-(diethylamino)-N-(4-((5-ethynyl-2,3-difluorophenyl)amino)-7-((tetrahydrofuran-3-yl)oxy)quinazolin-6-yl)but-2-enamide;

(S,E)-4-(diethylamino)-N-(4-((3-ethynyl-4,5-difluorophenyl)amino)-7-((tetrahydrofuran-3-yl)oxy)quinazolin-6-yl)but-2-enamide;

- (S,E)-4-(ethylamino)-N-(4-((3-ethynyl-4-fluorophenyl) amino)-7-((tetrahydrofuran-3-yl)oxy)quinazolin-6-yl)but-2-enamide;
- (S,E)-N-(4-((4-chloro-3-ethynylphenyl)amino)-7-((tetrahydrofuran-3-yl)oxy)quinazolin-6-yl)-4-(ethylamino)but-2-enamide;
- (S,E)-4-(ethyl(methyl)amino)-N-(4-((3-ethynyl-4-(trifluoromethyl)phenyl)amino)-7-((tetrahydrofuran-3-yl)oxy)quinazolin-6-yl)but-2-enamide; and
- (S,E)-N-(4-((4-cyano-3-ethynylphenyl)amino)-7-((tetrahydrofuran-3-yl)oxy)quinazolin-6-yl)-4-(ethylamino)but-2-enamide.

6. The compound of claim 5 or a pharmaceutically acceptable salt thereof, wherein the compound is (RS,E)-4-(diethylamino)-N-(4-((3-ethynylphenyl)amino)-7-((tetrahydrofuran-3-yl)oxy)quinazolin-6-yl)but-2-enamide.

7. The compound of claim 5 or a pharmaceutically acceptable salt thereof, wherein the compound is selected from the group consisting of
- (S,E)-4-(diethylamino)-N-(4-((3-ethynylphenyl)amino)-7-((tetrahydrofuran-3-yl)oxy)quinazolin-6-yl)but-2-enamide; and
- (R,E)-4-(diethylamino)-N-(4-((3-ethynylphenyl)amino)-7-((tetrahydrofuran-3-yl)oxy)quinazolin-6-yl)but-2-enamide.

8. The compound of (S,E)-4-(diethylamino)-N-(4-((3-ethynylphenyl)amino)-7-((tetrahydrofuran-3-yl)oxy)quinazolin-6-yl)but-2-enamide.

9. A pharmaceutical composition comprising a compound of claim 1 or a pharmaceutically acceptable salt thereof and a pharmaceutically acceptable carrier.

* * * * *